United States Patent [19]

Van den Engh et al.

[11] Patent Number: 4,770,992

[45] Date of Patent: Sep. 13, 1988

[54] DETECTION OF SPECIFIC DNA SEQUENCES BY FLOW CYTOMETRY

[76] Inventors: Gerrit J. Van den Engh; Barbara J. Trask, both of 699 Jefferson, Livermore, Calif. 94550

[21] Appl. No.: 802,802

[22] Filed: Nov. 27, 1985

[51] Int. Cl.[4] .............................................. C12Q 1/68
[52] U.S. Cl. .......................................... 435/6; 935/78; 436/800; 436/805
[58] Field of Search ............... 435/6; 935/78; 436/800, 436/805

[56] References Cited

U.S. PATENT DOCUMENTS 4,585,736  4/1986  Dolbeare et al. ...................... 935/77

OTHER PUBLICATIONS

Bernheim et al., Proc. Natl. Acad. Sci (USA) 80, pp. 7571-7575, (1983).
Trask et al., Science 230, pp. 1401-1403, Dec., 1985.

Primary Examiner—Robert J. Warden
Assistant Examiner—Robert Benson
Attorney, Agent, or Firm—Robert M. Hallenbeck

[57] ABSTRACT

A method for detection of DNA sequences. In the method, chromatin (comprising protein and DNA) is contacted with a cross-linking agent for the protein of the chromatin to provide a substantially rigid chromatin particle. The DNA of the chromatin particle is then subjected to treatment to cause a separation of the individual DNA strands into single stranded DNA. Preselected sequences of the single stranded DNA are then contacted with a complementary polynucleotide probe specific for the DNA sequence of interest. The polynucleotide probe is marked with a fluorescent label thereby labelling a target sequence of DNA in the chromatin particles. The fluorescently tagged DNA sequences are then detected by subjecting the polynucleotide probe to a suitable light source and detecting the light emitted by the fluorescent label so as to identify the preselected DNA sequence.

17 Claims, No Drawings

DETECTION OF SPECIFIC DNA SEQUENCES BY FLOW CYTOMETRY

BACKGROUND OF THE INVENTION

1. Field of the Invention

The present invention relates generally to a method for the detection of DNA sequences. More particularly, the present invention provides a method for the detection of DNA sequences through in situ hybridization and subsequent detection by flow cytometry.

The total length of the DNA helix present in the nucleus of each mammalian cell has been calculated to be about two meters. Under the influence of certain proteins, the DNA of the nucleus is packed into a sphere 5–10 um in diameter. The complex of DNA and protein is called chromatin. Shortly before a cell divides, the DNA becomes even more tightly coiled and is divided into a number of separate, compact packages, which can be observed under the microscope. These are called chromosomes. The number and size of the chromosomes are well-defined for each mammalian species. Human mitotic cells contain 46 chromosomes ranging in size from 2 to 10 $\mu$m.

Chromosomes carry the genetic information of a cell. The sequence of the nucleotide bases, which make up the DNA molecule, codes for the required proteins of the species. Each cell of the body contains a complete copy of the DNA and, therefore, a complete set of genetic instructions. The stretches of DNA that code for single hereditary characteristics are called genes. One chromosome may contain thousands of genes. At a given moment, only a small fraction of the genetic material is being translated. The location of the genes on the chromosomes and in relation to regulating sequences is important for their expression in the active genome. Changes in the sequence of the DNA, such as deletions or translocations, may have serious consequences for cell function, and ultimately for the health of the organism. Occasionally, changes in the DNA sequence, and in the protein for which it codes, can be advantageous.

One aspect of the organization of chromosomes of many species can be made visible under the microscope. Special staining techniques produce a striped pattern along the length of the chromosomes. These bands can be seen at high magnification through a microscope. Each chromosome has a characteristic banding pattern. The pattern provides a basis for the identification of the chromosomes. These staining procedures, and more elaborate techniques capable of producing more than 6000 bands in the human genome, have made it possible to detect the structural rearrangements in chromosomes that are reflected in abnormal banding patterns. Chromosomal rearrangements and variations in chromosome number have been associated with various cancers and inheritable human disorders. Radiation, chemical mutagens and viruses have been shown to produce lesions in chromosomes.

Various techniques have made it possible to progress from the study of banding patterns to the study of the molecular organization of chromatin. At a structural level, X-ray diffraction, electron microscopy and antibody labeling are a few of the techniques being used to unravel the 3-dimensional organization of histones, non-histone proteins, and DNA in chromatin and chromosomes.

Knowledge of the organization of chromosomes at the level of the nucleotide sequence itself is increasing at a rapid rate. The sequence, location, and regulation of genes, as well as the protein products of genes, can be studied with the introduction of techniques grouped under the term recombinant DNA technology. These include restriction enzyme digestion, DNA cloning and nucleic acid hybridization. DNA fragments can be multiplied (cloned) by inserting them into plasmids or bacterial viruses, which are then grown in bacteria. An endless variety of DNA sequence probes can be produced in pure quantities in this way. The cloned DNA sequences can also be used to construct a map of the genome in cells and chromosomes.

Using restriction enzymes, the organization of genes in the genome can also be studied. DNA is cut by these enzymes at very specific sites. The resulting DNA fragments are separated by gel electrophoresis. Gene sequence probes are matched by Southern blot hybridization to the highly specific restriction fragment patterns in these gels. For nucleic acid hybridization, the DNA is denatured, or separated into single strands. Under suitable conditions, DNA sequence probes will reanneal with the single stranded DNA to form double-stranded complexes where the nucleotide sequence of the probe and the denatured DNA match well, or are complementary. If the probe is radioactively labeled, the position of the hybridized probe can be visualized by autoradiography. Probes that overlap a splicing point help to link the fragments together in the construction of a complete sequence. In these restriction maps, the molecular organization in normal and abnormal cells of different species can be compared.

Because nucleic acid sequences occupy precise positions in cells and chromosomes, a great deal of information is lost when these molecules are extracted from cells by homogenization. New techniques make it possible to determine the location of specific DNA sequences in chromosomes. In this way, a link can be made between the genomic map and classical cytogenetics. Because chromosomes form a discrete subdivision of the total genome, they can be physically separated. Gene sequence probes can be hybridized in Southern blots or on filters to the DNA isolated from suspensions enriched for individual chromosome types. This is a rapid means of assigning genes to the chromosomes on which they reside.

DNA sequences can be more precisely located in chromosomes using a technique called in situ hybridization. In this technique, the nucleic acid sequence probes are hybridized to chromosomes fixed to slides, after the slide has been exposed to conditions which separate the base pairs in the DNA helix. The specific locations of the bound probe on the arms of the chromosomes can be visualized using radioactive, fluorescent, or enzymatic labeling procedures. The location of the sequences can also be determined in altered chromosomes present in abnormal cells.

Alternatively, purified fractions of a given chromosome can be used as the starting material for the cloning of DNA fragments using recombinant DNA techniques. A set of cloned DNA fragments is called a library. One can obtain, for instance, a library from the X or Y chromosome. Pre-enrichment of a given chromosome before cloning greatly simplifies the search for clones producing DNA sequences unique to that chromosome. "Walking" along the genome, or using overlapping DNA sequence probes to sequentially identify neighboring sequences, is easier when DNA from a single chromosome type has been cloned. Chromosome-specific probes are also useful tools in in situ hybridization studies for the identification of chromosomes, even when they are translocated to a new position, and for the enumeration of chromosomes. Recombinant clones prepared from defective chromosomes can also be a source of probes. These probes can be used to study the defect at a molecular level or to study the disorder's consequences for gene products and cell function.

The foregoing discussion illustrates that there are now many techniques with which chromatin and the genome can be studied. The techniques fall into two general classes: (1) those in which the properties of a population of cells or chromosomes, as a whole, can be characterized; and (2) those that allow the analysis of individual cells or chromosomes, but require their microscopic observation. When the properties of entire populations are averaged, as in the first group of techniques, information about any heterogeneity among the cells or chromosomes is lost. On the other hand, the analysis of individual cells or chromosomes with a microscope is still slow. Without microscope-based microfluorimeters, the observations are difficult to quantify, making them often subjective.

In recent years, flow cytometry instruments have been developed that make it possible to rapidly quantify the optical properties of individual cells, as well as to separate and purify selected cells. The technique of flow cytometry has also been extended to the analysis of chromosomes. If the molecular properties of chromosomes and/or the DNA of the cell nuclei can be successfully translated into optical properties, this technique offers a combination of features that have limited other techniques in the analysis of the genome.

For flow cytometric analysis, cells or cell fragments are suspended in solution and are stained with fluorescent dyes. In the flow cytometer, cells are forced in a narrow stream through the path of an intense light source, such as a laser. The particles pass the laser beam in single file at a rate of several thousand per second. When the cells enter the light spot, they scatter light or emit fluorescence. As each particle passes through the light source, its optical properties are quantified and stored. Large numbers of cells can be measured individually, and the optical properties of a cell population can be determined in a short time. Many flow cytometers also have the ability to sort cells. For this purpose, the sample stream is broken into droplets after the point where the optical measurements are performed. Droplets containing desired cells are given an electric charge and are deflected into a collection tube by the influence of an electrostatic field.

One of the applications of flow cytometry is the measurement of the DNA content of individual cells. During the cell cycle, an accurate copy of the DNA in a cell is made. When a cell divides, the two daughter cells each receive one copy of the DNA. If a population of cells is stained for total DNA content using a DNA-specific fluorchrome, the fluorescence intensity and, thus, the total DNA content, of each cell can be measured in a flow cytometer. Fluorescence distributions can be measured. The amount of DNA in each cell indicates its position in the cell cycle. Therefore, the distribution of cells among the cell cycle phases can be assessed from the form of the DNA fluorescence distribution. The presence of cells containing an abnormal amount of DNA (which may be due to an extra chromosome or to a chromosome of abnormal size) will also be reflected in the DNA distribution.

At mitosis, the DNA in a nucleus is partitioned over the chromosomes. If the chromosomes are released from mitotic cells, stabilized in solution and stained with fluorescent dyes, they too can be measured in a flow cytometer. Because chromosomes have only a fraction of the DNA content of whole nuclei, the measurement requires equipment with a high degree of sensitivity and precision. The peaks represent individual chromosomes. For this species, all the chromosomes are resolved. The relative peak positions in the distribution contains information about the set of chromosomes in the cells.

Several properties of flow cytometry make it a unique tool for cell biologists. The optical properties of individual cells or chromosomes are analyzed. These properties are expressed in a quantitative and objective manner. High measurement precision allows the detection of small differences in the number of fluorescent molecules bound to each particle in a suspension. Furthermore, the measurements can be performed rapidly. Analysis rates of 1000 events per second are normal, and rates up to 20,000 events per second have been reported. In addition, particles can be sorted from the others in a suspension on the basis of their optical properties for subsequent biochemical or biological assays. Chromosomes, for example, can be purified to be used in gene mapping or cloning experiments.

The application of flow cytometry to the study of cells and chromosomes is constrained by several conditions. To be quantified, a given biological property must be translated into an optical phenomenon, such as fluorescence or scattered light. Thus, a component of interest can be quantified by flow cytometry only when it can be suitably converted into an optical phenomenon. Fluorescent labels and assays have allowed the flow cytometry quantification of such diverse cellular properties as intracellular pH, membrane fluidity, DNA content, protein content, and the presence of membrane antigens. The second constraint is that the cells or chromosomes must exist as individual entities in suspension. This places restrictions on the handling of the particles prior to analysis. Many labeling procedures have been developed for cells or chromosomes fixed firmly to slides. Without this structural support, the cellular components fall apart during many procedures. Thirdly, to obtain relevant biological information from the fluorescence signals of each particle, these signals must be accurately quantified. Variation in the fluorescence intensities of identical particles must be minimized through optimal preparation and staining.

The present application relates to the use of flow cytometry to the study of the structure and molecular organization of the DNA of cell nuclei and chromosomes. The invention provides a method to treat chromatin so that the chromatin can be fluorescently labeled for quantification using flow cytometry. A technique is presented for the stabilization of chromatin in nuclei and chromosomes which allows in situ hybridization to be performed in suspension. A consequence of the method is the detection of specific DNA sequences in interphase nuclei using dual beam cytometry. The properties of the cell that can be analyzed include DNA content, specific DNA sequences base composition and interaction between DNA-specific dyes. Chromosomes derived from clinical material can be analyzed on the basis of these properties.

It would therefore be of great value to provide a method for the detection of DNA sequences nuclei and chromosomes by flow cytometry. For commercial applications, it would be desirable to provide prepared kits containing reagents which are standardized and optimized for sensitivity and accuracy for use in the detection of DNA sequences by flow cytometry.

2. Description of the Prior Art

U.S. Pat. No. 4,358,535 to Falkow et al describes a basic technique for in situ hybridization to determine DNA sequences. In accordance with the method, polynucleotide probes (DNA probes) specific for a DNA sequence (gene) encoding a product characteristic of a pathogen is labeled with a detectable label. A sample suspected of containing a pathogen is transferred onto an inert support, for example, a nitrocellulose filter. The sample is treated in such a way that the cells are localized. The cells are then treated so as to release their DNA and cause it to couple onto the support. Such treatment, as described in the Falkow patent results in the destruction of the cell membrane and the disruption of the nucleus. Subsequent treatment causes a separation of the individual strands of the genome. The strands are then contacted with polynucleotide probes specific for the characteristic polynucleotide sequence under hybridization conditions. Hybridization of the probe to the single stranded polynucleotides from the pathogen is detected by means of the label. The method described in the Falkow patent is suitable for macroscopic examination of DNA sequences but could not be used to examine the DNA sequences by flow cytometry.

SUMMARY OF THE INVENTION

The present invention is directed to a method for detection of DNA sequences. In the method, chromatin (comprising protein and DNA) is contacted with a cross-linking agent for the protein of the chromatin to provide a substantially rigid chromatin particle. The DNA of the chromatin particle is then subjected to treatment to cause a separation of the individual DNA strands into single stranded DNA. Preselected sequences of the single stranded DNA are then contacted with a complementary polynucleotide probe specific for the DNA sequence of interest. The polynucleotide probe is marked with a florescent label thereby labelling a target sequence of DNA in the chromatin particles. The fluorescently tagged DNA sequences are then detected by subjecting the polynucleotide probe to a suitable light source and detecting the light emitted by the florescent label so as to identify the preselected DNA sequence.

DESCRIPTION OF THE SPECIFIC EMBODIMENTS

In accordance with the present invention, a complex of DNA and protein (referred to herein as chromatin) is contacted with a cross-linking agent for a polar group of an amino acid of the protein in the chromatin. Amino acids containing polar groups which can be utilized for cross-linking include serine, glycine, aspartate, asparagine, glutamate, glutamine, lysine, arginine, tyrosine, histidine and tryptophan. In some instances the non-polar amino acid cysteine can be utilized for cross-linking through the sulfhydro group of cysteine. The cross-linking agent is a multi-functional compound having functional groups capable of reacting with a functional group on the polar amino acids. It has been determined that a preferred cross-linking agent is a diimidate having the formula;

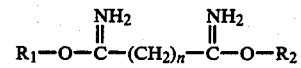

Wherein $R_1$ and $R_2$ are selected from methyl, ethyl and propyl and n is an integer from 1-10. A particularly preferred cross-linking agent is dimethyl suberimidate where n=6.

Prior to treatment with the cross-linking agent, the nuclei of the cells are isolated under conditions whereby the chromatin of the nuclei is stabilized. These conditions include treatment with a multivalent cation, particularly a divalent cation from the alkaline earth series. Particularly preferred is the use of magnesium ion. Most particularly, it is preferred to isolate the nucleus of the cells using a swelling buffer containing from about 25 to about 150 mM of a monovalent cation, such as potassium, from about 2 to about 20 mM of a divalent cation such as magnesium and which is buffered at a pH from about 7.5 to about 8.5. The divalent cation serves to stabilize the chromatin in the nucleus until the cross-linking agent can be used to fix the protein in the form of a particle.

The cross-linking agent is added to the nuclei protein at a level of from about 1 to about 10 mM. The cross-linking agent is preferably added in combination with a stabilizing salt, such as potassium carbonate. The pH of the cell suspension during treatment with the cross-linking agent is preferably from about 9 to about 11. The protein of the nuclei is preferably incubated with the cross-linking agent for a period of from about 10 minutes to about 1 hour.

After the nuclei has been separated from the cell membrane and incubated with the cross-linking agent, the protein particles formed can be treated by any suitable denaturation method to denature the DNA. To demonstrate that nuclei pretreated with a cross-linking agent are still suitable for in situ hybridization, mouse thymocyte nuclei which had been treated with dimethyl suberimidate where hybridized with a probe for mouse satellite DNA sequences. The nuclei were treated with various materials to denature the DNA to provide single stranded DNA to demonstrate that DMS treated nuclei remain intact under DNA denaturing conditions. The results with various denaturation buffers are shown herein below in Table 1.

The mouse satellite DNA sequences comprise approximately 10% of the total DNA in mouse nuclei. Total human DNA served as a control; this material shows no cross-hybridization to mouse DNA on filters or slides. The DNA probes were fluorescently labeled with the 2-acetyl aminofluorene procedure described in Landegent et al, Exp. Cell Res. 153: 61-72 (1984). Approximately 20% of the quanine residues in the DNA probes were chemically modified with acetoxy-2-acetyl aminofluorene (AAF). Nuclei, suspended in hybridization buffer in the presence of the AAF-labeled probe were denatured and incubated at the hybridization temperature overnight. After hybridization, the bound probe was detected with a rabbit anti-AAF antibody and a goat-anti-rabbit immunoglobulin conjugated to rhodamine.

TABLE 1

| treatment | no DMS | DMS |
|---|---|---|
| none | ++ | ++ |
| 100° C. 10 min. + Mg$^{++}$ | ++ | ++ |
| 100° C. 10 min. − Mg$^{++}$ | − | ++ |
| 2 × SSC. + Mg$^{++}$ | + | ++ |
| 2 × SSC. − Mg$^{++}$ | − − | ++ |
| 2 × SSC. 100° C. 10 min. + Mg$^{++}$ | ++ | ++ |
| 2 × SSC. 100° C. 10 min. − Mg$^{++}$ | − − | ++ |
| 50% formamide, 70° C., 10 min + Mg$^{++}$ | ++ | ++ |
| 50% formamide, 2 × SSC. +/− MG$^{++}$ | − − | ++ |
| 50% formamide, 2 × SSC. 70° C., + Mg$^{++}$ | − − | + |
| 0.07 NaOH, 25° C., 2 min | − − | − − |

++ = excellent; + = good; − = poor; − − = very poor

The amount of DNA probe required to hybridize with the number of nuclei routinely used in flow cytometry, i.e., about $10^6$, is more than most DNA chemists desire to use on a routine basis. Without scaledown, about 12 micrograms would be required for the necessary amount of hybridization probe. For this reason, it is usually desired to scale down the required number of hybridized particles to require only about 10–20 thousand hybridized nuclei particles and a hybridization volume of about 50 microliters. Accordingly, it is desirable to provide a deluent or filler particle to reduce the number of hybridized nuclei that are required. A suitable and preferred filler particle is an erythrocyte which has been cross-linked in accordance with the procedures described in this application. The erythrocytes are simply incubated with a suitable cross-linking agent, such as dimethylsuberimidate, so as to cross-link the protein of the erythrocyte. The erythrocytes are then combined with the hybridized nuclei particles at a suitable level prior to examination of the hybridized particles in a flow cytometer. In general, the cross-linked erythrocytes are combined with hybridized nuclei particles at a ratio of about 100:1 to about 1000:1 of filler particle to hybridized particle; preferably at a ratio of from about 300:1 to about 700:1.

The polynucleotide probe useful in the present invention may be any of the polynucleotide probes previously developed and known. The polynucleotide probe can be marked with a fluorescent marker by any suitable means. The probe can be directly marked by conjugation to a fluorescent marker or can be indirectly marked by modification of the DNA probe, such as by the incorporation of a ligand or hapten into the probe and recognition of the modified probe with an antibody or ligand coupled to a fluorescent label. Suitable haptens or ligands for the indirect fluorescent labelling of the probe include acetylamino fluorene (AAF), biotin, mercury and halodeoxyuridine. U.S. Pat. No. 4,529,700 to Gratzner describes a suitable monoclonal antibody for haleodeoxyuridine. Suitable fluorescent probes are described in U.S. Pat. No. 4,520,110 to Stryer et al. Other suitable fluorescent probes are commonly used fluorescent probes, such as fluorescein isothiocyanate and rhodamine.

The use of flow cytometry to determine DNA sequences in cells is a new approach. This approach offers advantages over alternative techniques, such as the isolation of DNA sequences and hybridization of the sequences on slides or paper. Large numbers of nuclei can be analyzed individually and rapidly, the distribution and relative amount of an DNA sequence and a heterogeneous population can be studied. The median of the fluoresence distribution of cell nuclei hybridized with the DNA probes complementary to 10% of the total genome is approximately 20 times higher than that of cell nuclei hybridized with a heterologous probe. This indicates that DNA sequences occurring at frequencies as low as 1% should be readily detectable by the method of the present invention. This level of sensitivity should allow the detection and enumeration, in interphase nuclei, of a given chromosome, amplified genes or viral sequences. The method of the invention is equally adaptable to the examination of chromosomal DNA and the total DNA of the cell nucleus.

The biochemical properties of chromosomes in suspension can be analyzed quantitatively with flow cytometry. The information that can be derived from the measured optical signals depends on the fluorescent labeling procedures that employed. Since the integrity of the chromosomes in suspension depends on the integrity of the DNA helix, labeling procedures that require strand separation cannot be applied directly. Studies of the nucleotide sequence in the DNA of chromosomes with base-specific antibodies or with DNA or RNA sequence specific probes, however, require strand separation. The present invention describes a technique for stabilizing the protein structure of chromosomes such that the DNA strands can be separated without affecting the integrity of the particles in suspension. This is done by cross-linking the proteins with dimethylsuberimidate (DMS). DMS is a cross-linking agent that reacts at high pH to form 10-nm bridges between protein molecules. The structural organization of chromosomes can also be preserved with DMS treatment to allow isolated chromosomes to be centrifuged onto microscope slides and banded for identification.

Strand separation in chromosomes is demonstrated using a monoclonal antibody against bromodeoxyuridine (BrdU) as described in the Gratzner patent. If cells are grown in its presence, BrdU is incorporated in place of thymidine during DNA synthesis. Anti BrdU antibody recognizes BrdU only in single-stranded DNA and requires the denaturation of chromatin to effect binding. This property makes the anti-BrdU antibody an ideal immunological reagent for assaying single strand formation in chromosomes.

The following examples further illustrate various features of the invention but are intended to in no way limit the scope of the invention which is defined in the appended claims.

EXAMPLE 1

The following example illustrates that the conformational state of DNA in individual chromosomes can be assayed using flow cytometry and an indirect immunofluorescence procedure employing the anti-BrdU antibody.

MATERIALS AND METHODS

Chromosome and nuclei preparation

Chromosomes were prepared from a Chinese hamster fibroblast culture derived from the M3-1 cell line. The cells were maintained in exponential growth. Chromosomes were isolated from mitotic cells. For some experiments, nuclei were isolated from the thymocytes of 6–8 wk old BC3 female mice.

Bromodeoxyuridine labeling

Where indicated, bromodeoxyuridine (BrdU, Sigma) was added to the culture medium of fibroblast cell lines 12 h before cell collection to a final concentration of 10 μM.

Dimethylsuberimidate (DMS) treatment

For DMS treatment, $K_2CO_3$ and DMS were added to a suspension of $5\times10^6$ nuclei/ml or approximately $5\times10^6$ chromosomes/ml from a concentrated stock solution mixed immediately before use. The final concentrations were 20 mM and 3 mM, respectively. The resultant pH was 10. After 15 min at 25° C., the pH was adjusted to 8.0 by the addition of 50 1 100 mM citric acid/ml. In some experiments, this process was repeated.

Denaturation and incubation in hybridization buffers

Salt or formamide was added to the chromosome suspensions as concentrations indicated below in Tables 2 and 3. SSC (Standard Saline Citrate) was added from a 20 times concentrated stock solution. 1×SSC is equivalent to 0.15M NaCl plus 0.015M Na-citrate. Formamide was added to final concentration of 50% (v/v) from a 100% solution (Kodak). The chromosomes were incubated at the temperatures indicated (where not specified 1 h, 25° C.) and diluted in isolation buffer containing $MgSO_4$ (IB+M, containing 50 mM KCL, 5 mM HEPES, and 10 mM $MgSO_4$) before being stained. Chromosome suspensions were incubated at the indicated temperatures in water bath.

Immunofluorescent labeling with anti-BrdU

Chromosomes were isolated from cells grown either in the presence or absence of BrdU as described above, with the exception that the reducing agent, dithiothreitol, was omitted from isolation buffer. The chromosomes were treated with DMS. Samples containing 0.5 ml chromosome suspension were used. In some experiments, formamide was added to 50% final concentration. After the chromosome suspensions were incubated in hot water baths at the temperatures indicated, the tubes were placed quickly on ice. Formamide-containing suspensions were diluted by adding an equal volume of cold IB+M. Anti-BrdU and FCS were added to 1:10 dilution and 2% final concentration, respectively. The suspensions were incubated 15 min at room temperature and subsequently centrifuged 15 min at 300 g. After removal of the supernatant fluid, the pellet was resuspended in 0.5 ml IB+M containing 2%, FC 0.25% Triton X-100, and a 1:10 dilution of anti-mouse immunoglobulin conjugated to fluorescein molecules (FITC). After incubation at room temperature for 15 min, the suspension was layered carefully on 1 ml IB+M containing 10% FCS and centrifuged 10 min at 300 g. The pellet was resuspended in 1.0 ml IB+M.

Flow cytometric analysis

Chromosome and nuclei suspensions were analyzed using the a dual beam cytometer. The amplifier gains were adjusted for the measurement of each panel to utilize the full 256 channels of the pulse height analyzer. The FITC fluorescence was measured using a logarithmic amplifier in which 20 channels is equivalent to approximately 5 to 10-fold difference in fluorescence intensity.

Effect of DMS treatment on chromosome stability

After DMS treatment, chromosomes in suspension can withstand conditions which denature the DNA helix. The effect of media and temperatures that are commonly used to induce strand separation for DNA-DNA hybridization experiments was determined. These protocols make use of buffers containing high salt and chelating agent concentrations (SSC) and formamide followed by incubation at high temperatures. Chromosomes were subjected to several of these procedures, and, after cooling, the chromosomes were stained with HO. A fluorescence distribution was measured for each suspension in a flow cytometer. The DNA distribution of untreated chromosomes shows significantly fewer resolved chromosomes and a higher debris level than that of DMS-treated chromosomes.

The effect of DMS treatment on the stability of chromosomes under a series of conditions as determined from the quality of the measured DNA distribution is summarized in Table 2. The results presented here indicate that DMS-treated chromosomes are stable under more harsh conditions than untreated chromosomes. Under some conditions, two repeated treatments with DMS are more effective for chromosome stabilization than a single treatment.

TABLE 2

EFFECT OF DMS TREATMENT ON THE ABILITY OF CHROMOSOMES TO WITHSTAND VARIOUS HYBRIDIZATION BUFFERS AND DENATURATION CONDITIONS AS MEASURED IN A FLOW CYTOMETER

| additions to medium and temperature | times treated with 3 mM dimethylsuberimidate | | |
|---|---|---|---|
| | 0 | 1 | 2 |
| none | ++ | ++ | ++ |
| 2 × SSC | + | + | + |
| 100° C., 10 min | − | + | + |
| 2 × SSC, 100° C., 10 min | −− | (−−) | + |
| 50% formamide | (−) | (+) | (+) |
| 50% formamide, 2 × SSC | − | (−) | + |
| 50% formamide, 70° C., 10 min | −− | − | + |
| 50% formamide, 2 × SSC, 70° C., 10 min | −− | (−−) | − |

++ = excellent; + = good; − = poor; −− = very poor. The judgements in parenthesis are based on chromosome morphology as observed with a light microscope.

Effect of salt and high incubation temperatures on DMS-treated chromosomes

The results in Table 2 indicate that DMA-treated chromosomes maintain their integrity under several conditions used for DNA denaturation. Chromosomes treated with DMS one time are not, however, maintained under conditions that combine high salt and chelating agent concentrations with high temperatures or with formamide. This was further investigated by examining the morphology of DMS-treated chromosomes with a fluorescence microscope after their incubation at several different temperatures in various SSC concentrations as shown in Table 3. As the salt and chelating agent concentrations are increased by the addition of 0 to 3×SSC, the temperature decreases at which chromosomes fall apart. These chromosomes swell substantially in 2–3×SSC at low temperatures, but remain intact. At higher temperatures, the chromosomes fall apart. In contrast, chromosomes treated twice with DMS can withstand the combination of 2×SSC and boiling. The results are shown in Table 3.

TABLE 3

EFFECT OF SSC* CONCENTRATION AND INCUBATION TEMPERATURES ON THE MORPHOLOGICAL INTEGRITY OF ISOLATED CHROMOSOMES TREATED WITH DIMETHYLSUBERIMIDATE (DMS)**

| temperature | 0 × SSC | 1 × SSC | 2 × SSC | 3 × SSC |
|---|---|---|---|---|
| 25° C., 2 h | ++ | ++ | +/− | +/− |
| 36° C., 2 h | ++ | ++ | ++ | ++ |
| 60° C., 2 h | ++ | ++ | +/− | −− |
| 80° C., 2 h | ++ | ++ | +/− | −− |
| 100° C., 3 min | ++ | ++ | −−(++) | −− |

TABLE 3-continued
EFFECT OF SSC* CONCENTRATION AND INCUBATION TEMPERATURES ON THE MORPHOLOGICAL INTEGRITY OF ISOLATED CHROMOSOMES TREATED WITH DIMETHYLSUBERIMIDATE (DMS)**

| temperature | 0 × SSC | 1 × SSC | 2 × SSC | 3 × SSC |
|---|---|---|---|---|
| 100° C., 10 min | ++ | +/− | −−(++) | −− |

++, chromosomes intact or only slightly swollen; +/−, chromosomes very swollen; −−, chromosomes have fallen apart into mass of chromatin, not recognizable as chromosomes. The observations in parenthesis are for two treatments with DMS.

Anti-BrdU labeling

An immunofluorescence labeling procedure and flow cytometry were employed to determine the extent of single strand formation in DMS-treated chromosomes exposed to conditions for DNA denaturation. Chromosomes were isolated from cells grown 12 h in the presence or absence of bromodeosyuridine (BrdU). The chromosomes were stabilized with DMS. The chromosome suspensions were denatured by boiling for 15 min and were quenched quickly on ice to minimize renaturation of the DNA helix. Chromosomes were labeled with a monoclonal antibody that recognizes BrdU only in single stranded DNA, followed by incubation with an anti-mouse immunoglobulin-FITC antibody. The DNA in the chromosomes was stained with PI. The FITC fluorescence intensity of BrdU-containing chromosomes is approximately 10 times higher than the fluorescence of chromosomes from cells not grown in BrdU.

DNA resolution after denaturation

The resolution of chromosomes in a DNA fluorescence distribution is well preserved despite DMS treatment, denaturation, and immunofluorescent labeling. The various chromosomes from Chinese hamster cells can be identified in this distribution.

Assay of single-strand formation

Anti-BrdU labeling can be used to compare the degree of single-strand formation in chromosomes incubated under various denaturation conditions. This chromosome can be easily recognized in the distributions by its DNA fluorescence intensity. The fluorescence intensity of BrdU-containing chromosomes is significantly higher if the chromosomes are boiled for 15 min, rather than 5 min, before immunofluorescent labeling. Boiling decreases the level of the specific fluorescence measured for chromosomes that do not contain BrdU. The fluorescence of BrdU containing chromosomes after denaturation at 80 C in 50% formamide is as high as that of the chromosomes boiled in IB+M for 15 min. However, the aspecific fluorescence of chromosomes that do not contain BrdU is significantly higher in the presence of formamide. Similar results were observed in three repeated experiments.

What is claimed is:

1. A method of detecting preselected DNA sequences in a chromatin particle by fluorescence activated flow cytometry or fluorescence microscopy comprising
   (1) contacting chromatin with a cross-linking agent for the protein of said chromatin to provide a substantially rigid chromatin particle;
   (2) subjecting the DNA of said chromatin particle to denaturing conditions so as to separate double stranded DNA into single stranded DNA;
   (3) contacting preselected sequences of said single stranded DNA with a nucleic acid probe complementary to said preselected DNA sequence;
   (4) marking said nucleic acid probe with a fluorescent label; and
   (5) detecting said marked nucleic acid probe by fluorescence activated flow cytometry or fluorescence microscopy so to identify said preselected DNA sequence.

2. A method in accordance with claim 1 wherein said detection is accomplished by passing said chromatin particle through a fluorescence activated flow cytometer.

3. A method in accordance with claim 1 wherein said detection is accomplished by means of a fluorescence microscope.

4. A method in accordance with claim 1 wherein said cross-linking agent is an organic compound having at least two functional groups which are reactive with the terminal functional groups of the polar amino acids of said protein of said chromatin.

5. A method in accordance with claim 1 wherein said cross-linking agent is a diimidate having the formula:

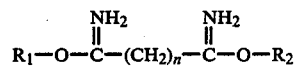

wherein $R_1$ and $R_2$ are selected from methyl, ethyl and propyl and n is an integer from 1 to 10.

6. A method in accordance with claim 5 wherein said cross-linking agent is dimethyl suberimidate.

7. A method in accordance with claim 1 wherein said chromatin particle is combined with an erythrocyte filler particle prior to said detection step.

8. A method in accordance with claim 7 wherein the ratio of said filler particles to said chromatin particles is from about 100:1 to about 1000:1.

9. A method in accordance with claim 7 wherein the ratio of said filler particles to chromatin particles is from about 300:1 to about 700:1.

10. A method in accordance with claim 7 wherein said filler particle has been contacted with a cross-linking agent for the protein of said erythrocyte.

11. A method in accordance with claim 10 wherein said cross-linking agent is an organic compound having at least two functional groups which are reactive with the terminal functional groups of the polar amino acids of said protein.

12. A method in accordance with claim 10 wherein said cross linking agent is a diimidate having the formula:

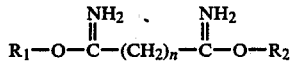

wherein $R_1$ and $R_2$ are selected from methyl, ethyl and propyl and n is an integer from 1 to 10.

13. A method in accordance with claim 10 wherein said cross-linking agent is dimethyl suberimidate.

14. A method in accordance with claim 1 wherein said nucleic acid probe is marked by labeling the nucleic acid probe with a hapten or ligand and thereafter incubating said hapten or ligand labeled probe with an anti-hapten or anti-ligand antibody coupled to a fluorescent label.

15. A method in accordance with claim 1 wherein said chromatin particle contains the total nuclear DNA.

16. A method in accordance with claim 1 wherein said chromatin particle is a chromosome.

17. A method of detecting preselected DNA sequences in a chromatin particle by fluorescence activated flow cytometry or fluorescence microscopy comprising:
  (1) contacting chromatin with a cross-linking agent for the protein of said chromatin to provide a substantially rigid chromatin particle,
  (2) subjecting the DNA of said chromatin particle to denaturing conditions so as to separate double stranded DNA into single stranded DNA;
  (3) contacting preselected sequences of said single stranded DNA with a nucleic acid probe complementary to said preselected DNA sequence, said nucleic acid probe being conjugated to a fluorescent label;
  (4) detecting said fluorescently labeled nucleic acid probe by fluorescence activated flow cytometry or fluorescence microscopy so to identify said preselected DNA sequence.

* * * * *